(12) United States Patent
Ding

(10) Patent No.: US 7,733,489 B2
(45) Date of Patent: Jun. 8, 2010

(54) OPTICAL METHOD OF MULTI-BAND MIXING

(75) Inventor: Fujian Ding, 9A, Parkway Rd., #102, Greenbelt, MD (US) 20770

(73) Assignee: Fujian Ding, Stillwater, OK (US)

(*) Notice: Subject to any disclaimer, the term of this patent is extended or adjusted under 35 U.S.C. 154(b) by 667 days.

(21) Appl. No.: 11/530,469

(22) Filed: Sep. 10, 2006

(65) Prior Publication Data

US 2008/0122709 A1    May 29, 2008

(51) Int. Cl.
    *G01N 21/85*      (2006.01)
(52) U.S. Cl. .................. 356/416; 356/407; 356/408
(58) Field of Classification Search ................ 356/416, 356/407, 408
See application file for complete search history.

(56) References Cited

U.S. PATENT DOCUMENTS

| | | | | |
|---|---|---|---|---|
| 6,075,661 A | * | 6/2000 | Gross et al. | ................ 359/819 |
| 2007/0052961 A1 | * | 3/2007 | Lane et al. | ................ 356/406 |

OTHER PUBLICATIONS

Fujian Ding et al, Applied Optics, Sep. 10, 2005, 5454-5462, 44(26), Optical Society of America.

Fujian Ding et al, Applied Optics, Feb. 1, 2006, 668-677, 45(4), Optical Society of America.

Fujian Ding et al, Applied Optics, May 20, 2006, 3516-3526, 45(15), Optical Society of America.

Fujian Ding et al, Optical Sensors and Sensing Systems for Natural Resources and Food Safety and Quality, SPIE, 5996(2005), Oct. 23, 2005, 59960R.

* cited by examiner

*Primary Examiner*—L. G Lauchman

(57) ABSTRACT

The color difference and/or chromaticness difference between target objects and background objects can be enhanced. Different colors with different color attributes mean different objects. In some cases, different chromaticness, such as saturation and hue, mean different two- or three-band ratio. The light from the surface of objects is filtered by optical system integrated with two- and three-band mixing method so that only the light in the wavelength range of the pass bands can reach optical sensors for opto-electronic sensing devices. With this kind of opto-electronic sensing devices, two- and/or three-band ratio criteria widely used in remote sensing and machine vision applications can be calculated in terms of color attributes. Multi-spectral imaging system can be replaced by this kind of sensing devices. This kind of two- or three-band mixing illumination can be used to identify, classify, and detect objects for human visual application, remote sensing, and machine vision application.

23 Claims, 13 Drawing Sheets

OPTICAL METHOD OF MULTI-BAND MIXING

BACKGROUND OF THE INVENTION

1. Field of the Invention

The invention relates to a novel and improved method and apparatus for filtering the light, or enhancing color difference and/or chromaticness difference, or obtaining two- or three-band ratio criteria widely used in remote sensing applications, or acquiring two or three bands multi-spectral imaging.

2. Description of the Prior Art

For applications of band ratio criteria, including two- and three-band ratio, multi-spectral imaging system, hyper-spectral imaging system, and spectral system are used in order to get different band spectral information. Then, two- or three-band ratio criteria with different indices, which are playing a very important role in the remote sensing application due to its invariant to some geometrical factors, such as distances between imaging system and objects, angle between the optical axis of optical system and normal lines to object surfaces, and the intensity change of illumination, can be calculated with mathematic processing.

Conventional multi-spectral imaging systems are used to get two or three bands imaging in applications, such as machine vision and remote sensing.

Several separate different band illuminations were adopted for some multi-band applications of color discrimination or object identification through color discrimination. In these kinds of applications, the lights from several separate different band illuminations illuminated the object's surface.

However, all the above sensing systems that can be used to obtain two- or three-band ratio criteria or to get two or three bands imaging are complicated and expensive to some extent due to their structure, manufacture, and calibration. For the beam-splitter multi-spectral imaging system, the multi-channel beam splitter, multi-optical-paths, the respective one-band filters, and the respective optical sensors are necessary for acquiring multi-spectral imaging. In the application of several separate different band illuminations, this illumination method for color discrimination is complicated and costly, and doesn't have a good illumination performance, and is not suitable for some applications.

SUMMARY OF THE INVENTION

I have now invented a novel and improved method for filtering the light, for enhancing color difference and/or chromaticness difference, for implementing two- and three-band ratio criteria, and for acquiring two or three bands multi-spectral imaging. This method can be used in visual device, such as (but not be limited to) binocular, monocular, telescope, microscope, and integrated in opto-electronic sensing devices, such as (but not be limited to) imaging systems, spectroscopy systems, and color-measuring systems, and can be used in illumination. In this process, there is only the light in the wavelength range of several bands with different central wavelengths can go through the optical system, or optical instrument, or illumination system and reach objects, or human eyes, or optical sensors. In this process, there are two ways of filtering the light from the light source to objects or the light from the objects to human eyes or optical sensors. The first way is with either a special two- or three-band bandpass filter or a special arrangement of several one-band bandpass filters integrated in the optical system. In this case, the sole role of the filter(s) is only filtering the light from lighting source to objects or the light from objects to human eyes or optical sensors. The second way is by coating some optical component of the optical system. Then this optical component has the function of filtering the light from the lighting source to objects illuminated or the light from objects to human eyes or optical sensors and the function of optical component in the optical system. Then only the light in the range of several bands of the filter or filters can reach the objects or be received by human eyes or optical sensors. And the mixing image of several bands can be acquired to human eyes or optical sensors. With optimization of several bands, the color difference and/or chromaticness difference between targets and backgrounds can be enhanced. Two- or three-band ratio criteria can be calculated in terms of color attributes of the mixing image of two or three bands respectively, such as (but is not limited to) saturation and hue of the color, for object classification or target identification. With these two- or three-band mixing images, two or three separate one-band images can be obtained with mathematics processing so that the conventional multi-spectral imaging system can be taken place by this kind of two- or three-band mixing device, which is simple and low-cost compared with conventional multi-spectral imaging systems.

In accordance with this discovery, it is an object of this invention to provide an improved method for filtering the light from lighting source to objects illuminated.

In accordance with this discovery, it is an object of this invention to provide an improved method for filtering the light from objects to human eyes or optical sensors.

In accordance with this discovery, it is an object of this invention to provide an improved method for enhancing color difference and chromaticness difference for color discrimination for some applications.

In accordance with this discovery, it is an object of this invention to acquiring two or three separate different central wavelength spectral imaging.

Yet another object of the invention is to provide an improved low cost, simpler method which is capable of implementing of two- and three-band ratio criteria in a novel way other than conventional ways of beam-splitting, beam-grating used in hyper-spectral, multi-spectral, and spectral systems.

Other objects and advantages of the invention will become apparent from the ensuing description.

BRIEF DESCRIPTION OF THE DRAWING

The following figures are intended only to further illustrate the invention and are not intended to limit the scope of the invention which is defined by the claims.

DETAILED DESCRIPTION OF THE INVENTION

The process of this invention can be integrated in illuminations.

The process of this invention can be integrated in visual devices, such as (are intended only to further illustrate the invention and are not intended to limit to) binocular, monocular, telescope, and microscope.

The process of this invention can be integrated in opto-electronic sensing systems, such as (are intended only to further illustrate the invention and are not intended to limit to) colorimeter, color camera, and spectral system.

Figure 1:
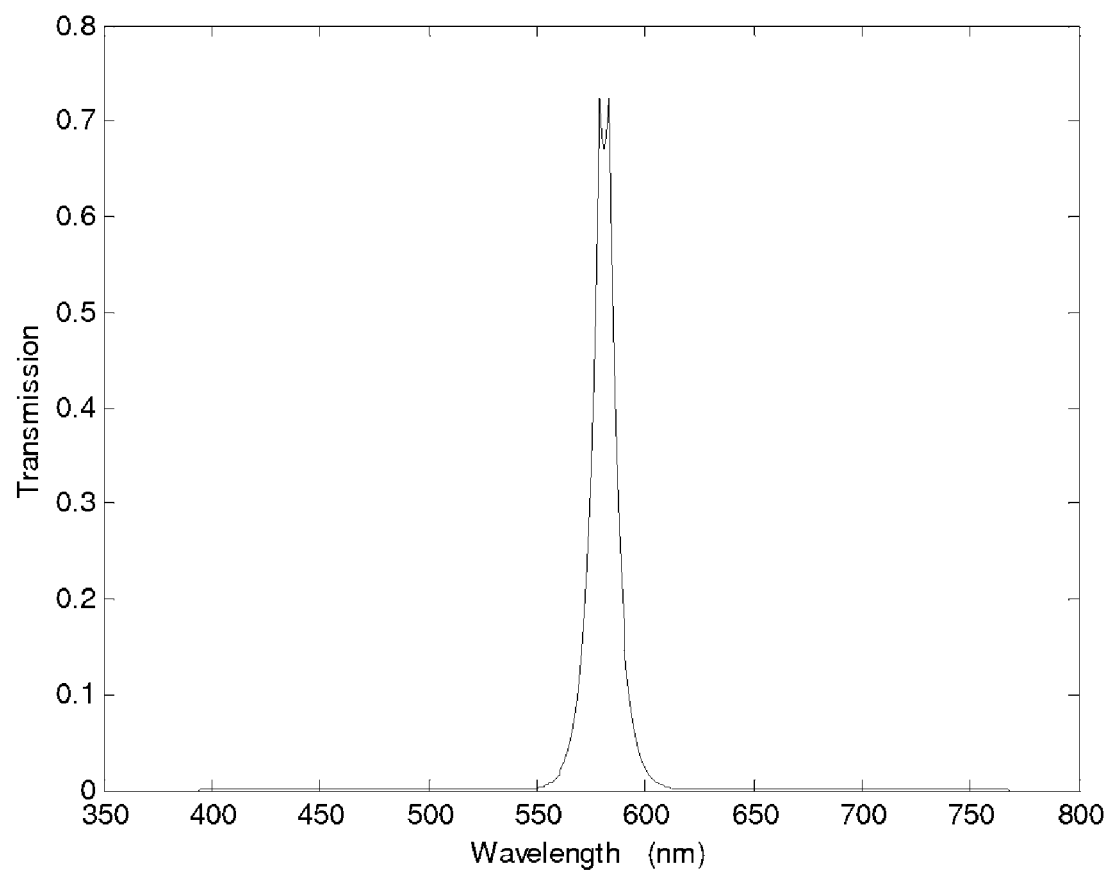
FIG. 1 is a schematic of the optical transmittance of one-band bandpass filter.
Figure 2:
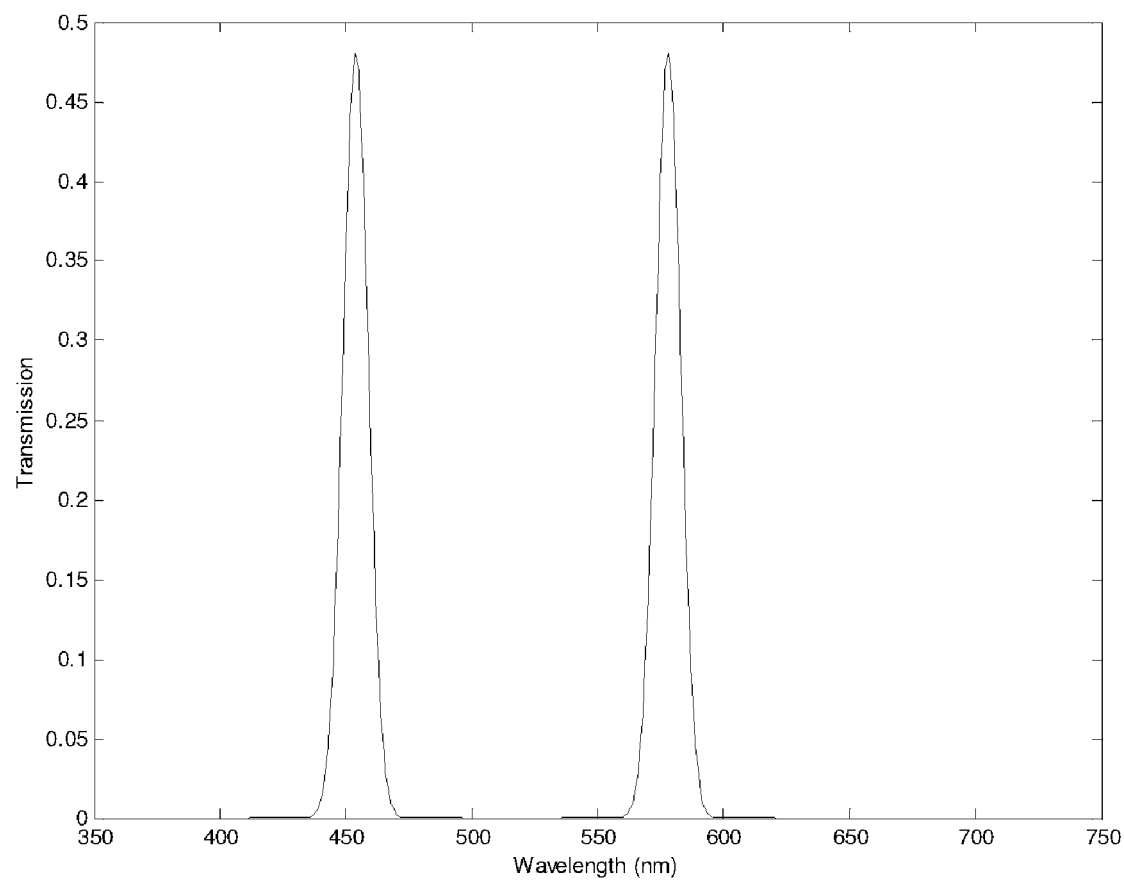
FIG. 2 is the schematic of the optical transmittance of two-band bandpass filter.
Figure 3:
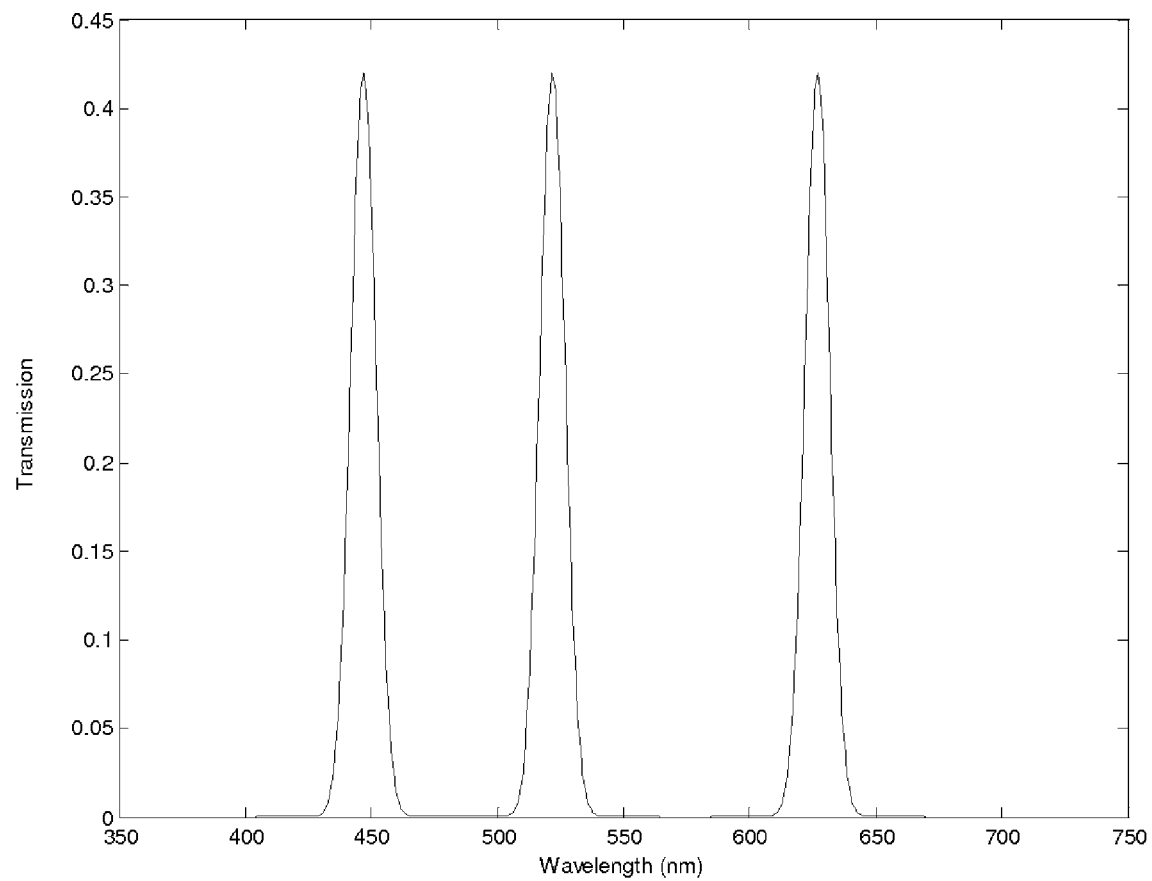
FIG. 3 is the schematic of the optical transmittance of three-band bandpass filter.

The process of this invention is implemented by integrating optical filter(s) in illumination, or optical system of opto-electronic sensing system, or visual optical instrument. The filter(s) integrated may be one-band bandpass filters (FIG. 1) of different central wavelengths, such as (but is not limited to) any kind of shape and size interference one-band narrow bandpass filters with different arrangement. The filter integrated may be any kind of shape and size special bandpass filter of two (FIG. 2) or three bands (FIG. 3). It is understood that the term any kind of shape and size as used herein encompasses products which may contain but not limit to any size of circular, rectangle, square, triangle, circle ring, ellipse, ellipse ring, trapezoid, and circular sector. And the filter(s) can be integrated in front of, behind, and in the middle of the optical system of the visual instrument, or opto-electronic sensing system, or illumination system.

Figure 4:
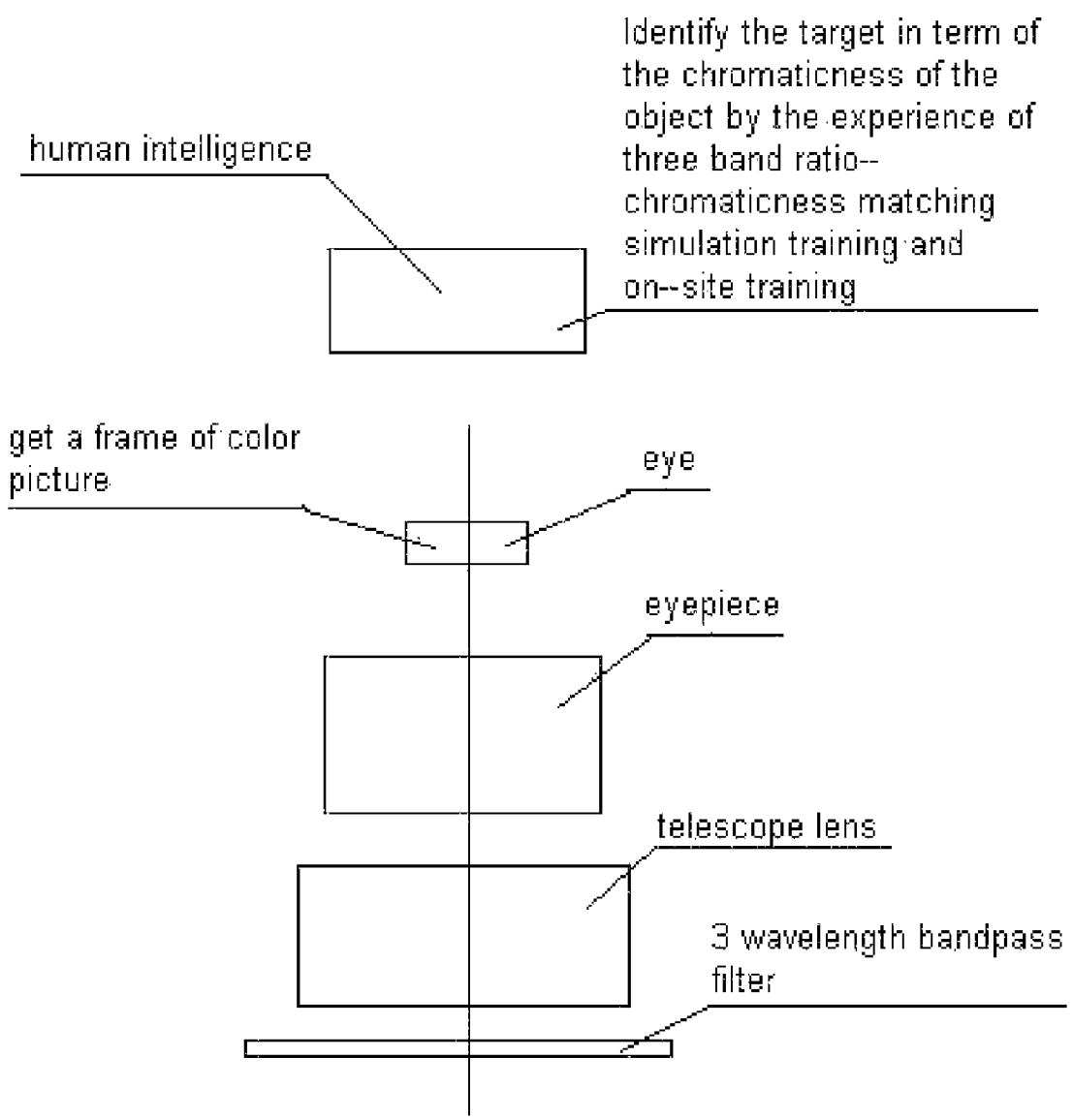
FIG. 4 is a schematic of a kind of three-band mixing binocular.

The filter(s) can be directly integrated in some commercial visual instrument or optical systems without any correction for optical aberrations. For example, the filter(s) can be directly installed in front of some commercial binoculars (FIG. 4).

The filter(s) can be integrated in some visual device and optical system with correction for optical aberrations. For example, if the kind of interference bandpass filter(s) is (are) used, then the collimating should be taken into account so that the angle of incidence to the interference bandpass filter(s) can be under the allowed tolerance.

The invention with different central wavelength one-band bandpass filters has a more applicable to the applications. Here, the central wavelengths of two or three bands can be changeable and low cost by changing different central wavelength filters. And the device can be used as either two-band mixing or three-band mixing with different filter arrangement for the same filter holder.

The invention with a two-band or three-band bandpass filter has a better optical quality to some extent compared with the invention with different central wavelength one-band bandpass filters. In this case, the wavelengths of two or three bands may be still changeable by changing the special two-band or three-band bandpass filter with different central wavelengths.

The process of this invention is implemented by coating some optical component(s) of the optical system so that this coated component can function as a filter as well as its other function in the optical system. It is understood that the term coating as used here encompasses any coating method used currently and in the future.

The process of invention by coating some optical component(s) of the optical instrument or optical system is implemented with custom-design. So the optical aberration can be taken into account for the specific waveband pair or waveband set. Generally speaking, the central wavelengths may not be changeable.

The determination of the central wavelengths of the filter(s) in accordance with this invention is important for the application background. For different applications, the related feasible wavebands are chosen in terms of different criteria, such as color difference, chromaticness difference. For the applications to replace the conventional multi-spectral imaging system and to implement the two- or three-band ratio, the wavebands can be any bands required for the related applications.

The target identification with two- or three-band mixing visual device is based on the operator's knowledge of it. The operator can identify target objects and background objects in terms of their color or chromaticity difference, which is enhanced by this visual device, such as the differences of saturation, hue, and/or brightness between perceived objects.

The target identification with two- or three-band mixing opto-electronic sensing device is implemented in two following ways. First, this two- or three-band mixing electronic devices only provides the enhanced color images to the inspectors for their manual monitoring. Second, this two- or three-band mixing sensing device provides the mixing color images to intelligent device, such as computers and microprocessors, for the automatic inspection. Then, the intelligent device can identify and classify the objects in term of their color attributes. If necessary, the intelligent device can calculate the two- or three-band ratio in terms of color attributes. It is understood that the term automatic inspection as used herein encompasses but not limits to automatic target identification or detection, industry inspection or monitoring, object identification and classification, quality inspection and grading.

It is understood that the foregoing detailed description is given merely by way of illustration and that modifications and variations may be made therein without departing from the spirit and scope of the invention.

The following examples are intended only to further illustrate the invention and are not intended to limit the scope of the invention which is defined by the claims.

Example 1

Figure 5:
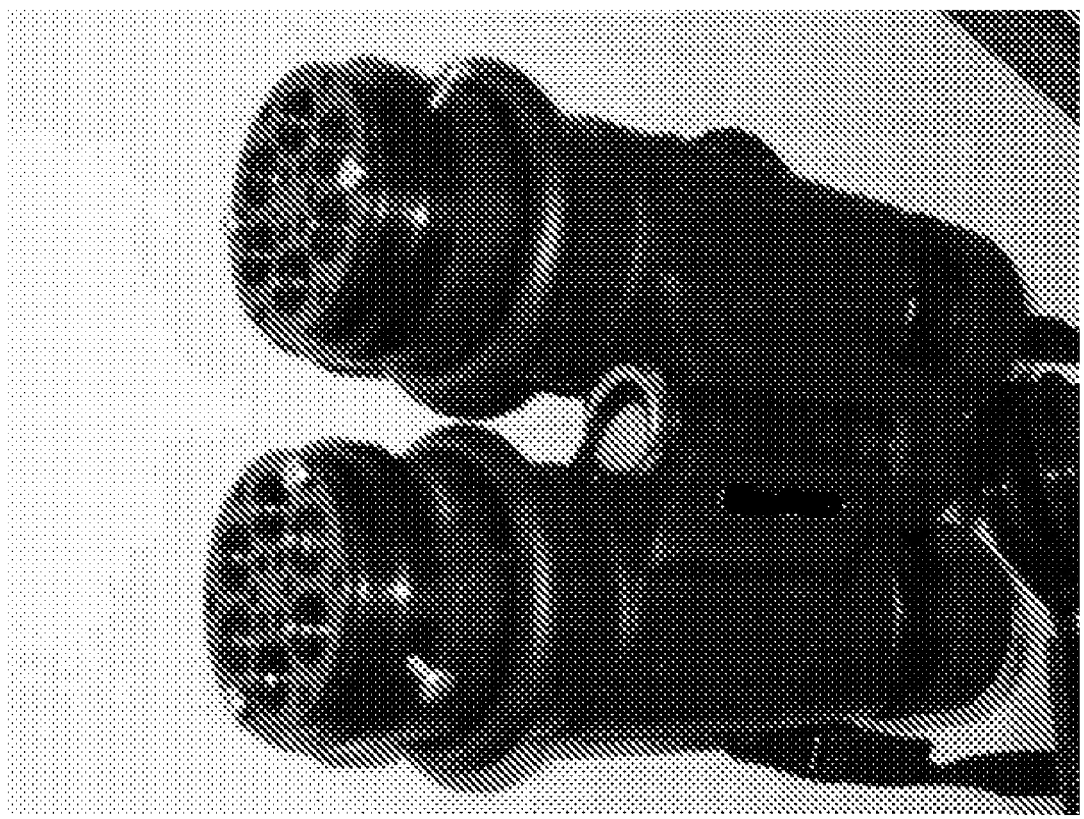
FIG. 5 is a photographic image of a kind of prototype of band-changeable two- and three-band mixing binocular based on the band mixing technology.
Figure 6:
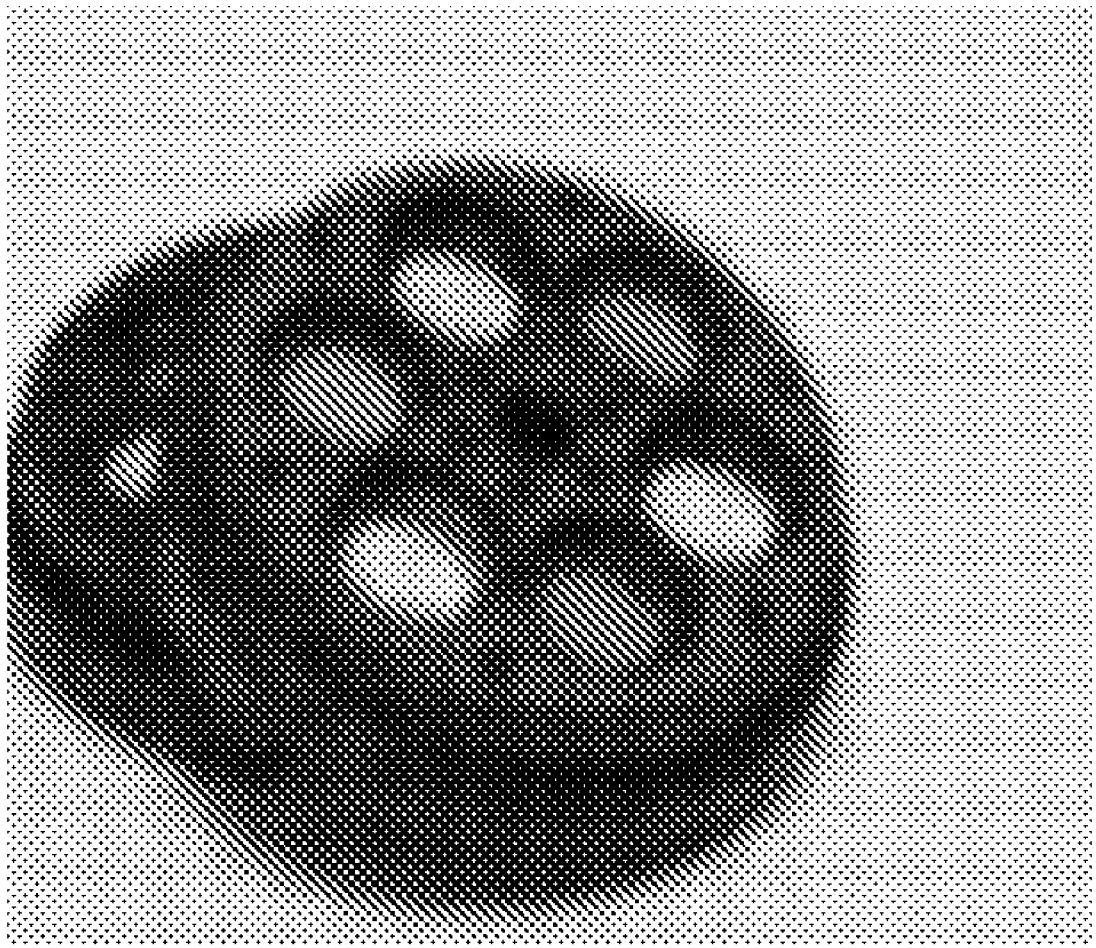
FIG. 6 is a photographic image of a specific filters arrangement for two-band mixing application of a kind of prototype of band-changeable two- and three-band mixing binocular based on the band mixing technology.
Figure 7:
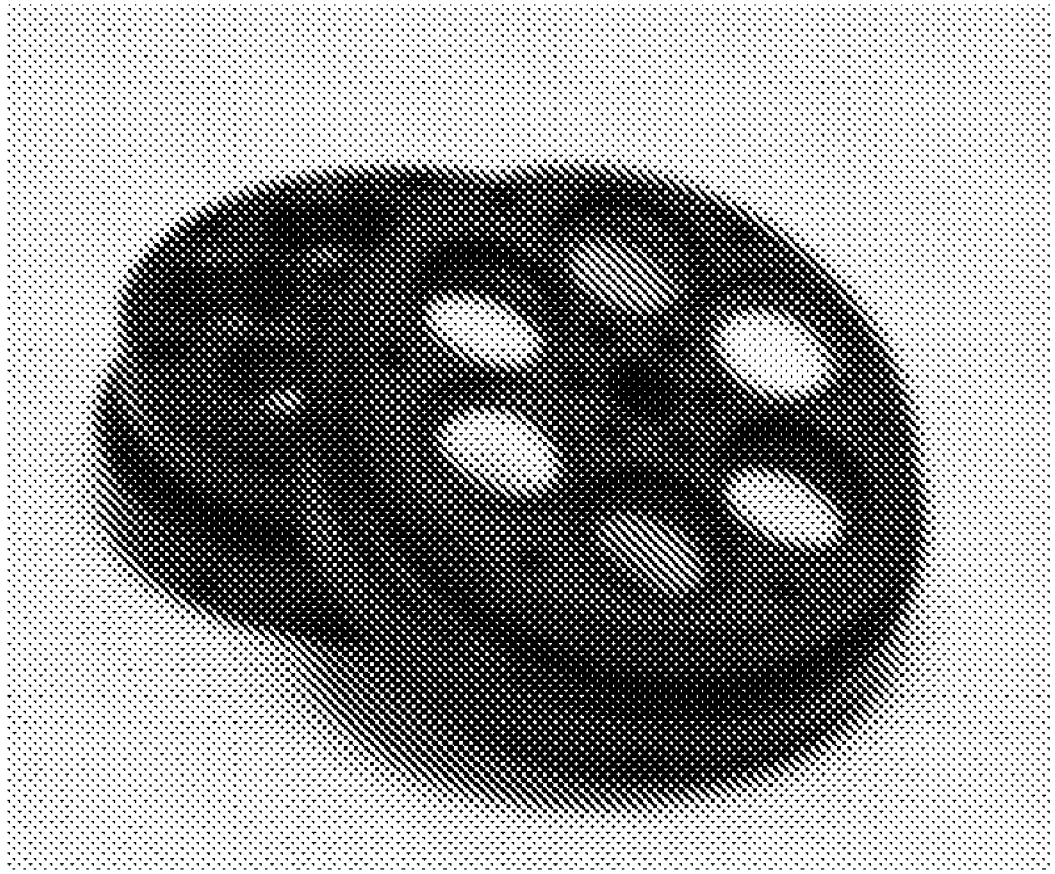
FIG. 7 is a photographic image of a specific filters arrangement for three-band mixing application of a kind of prototype of band-changeable two- and three-band mixing binocular based on the band mixing technology.
Figure 8:
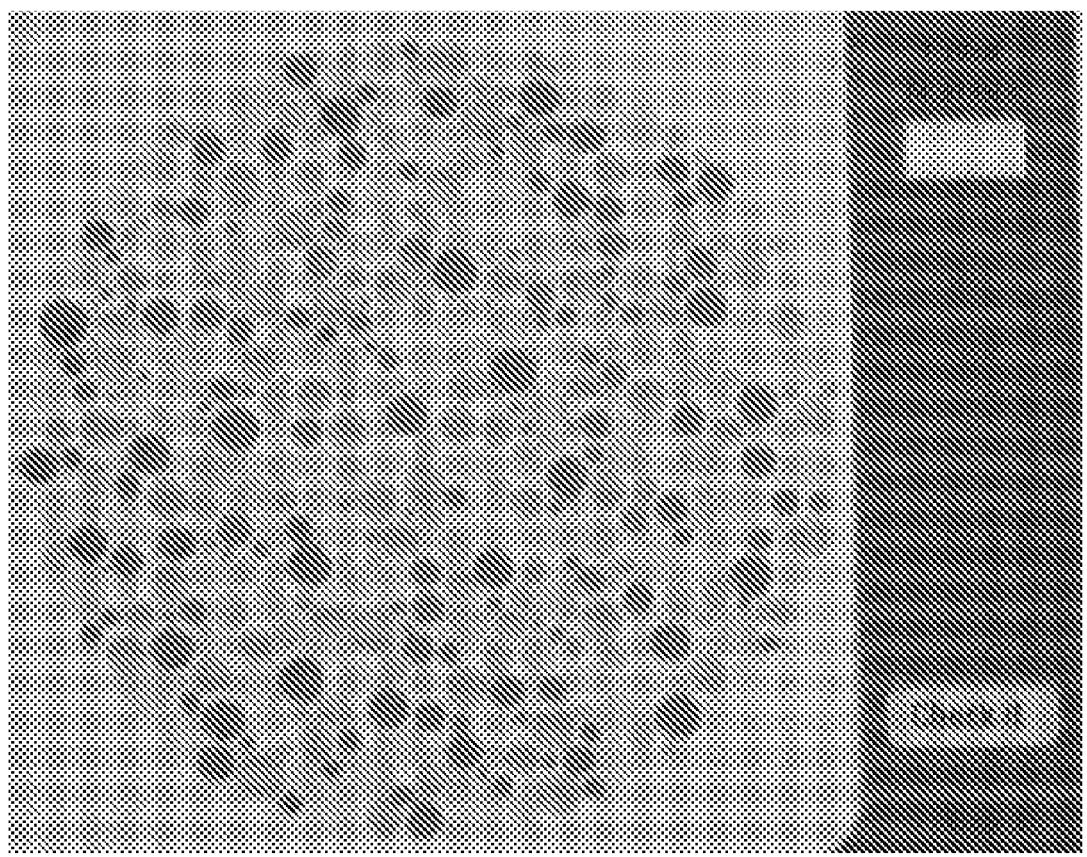
FIG. 8 is a photographic image of a color blindness test card with target number of 73.
Figure 9:
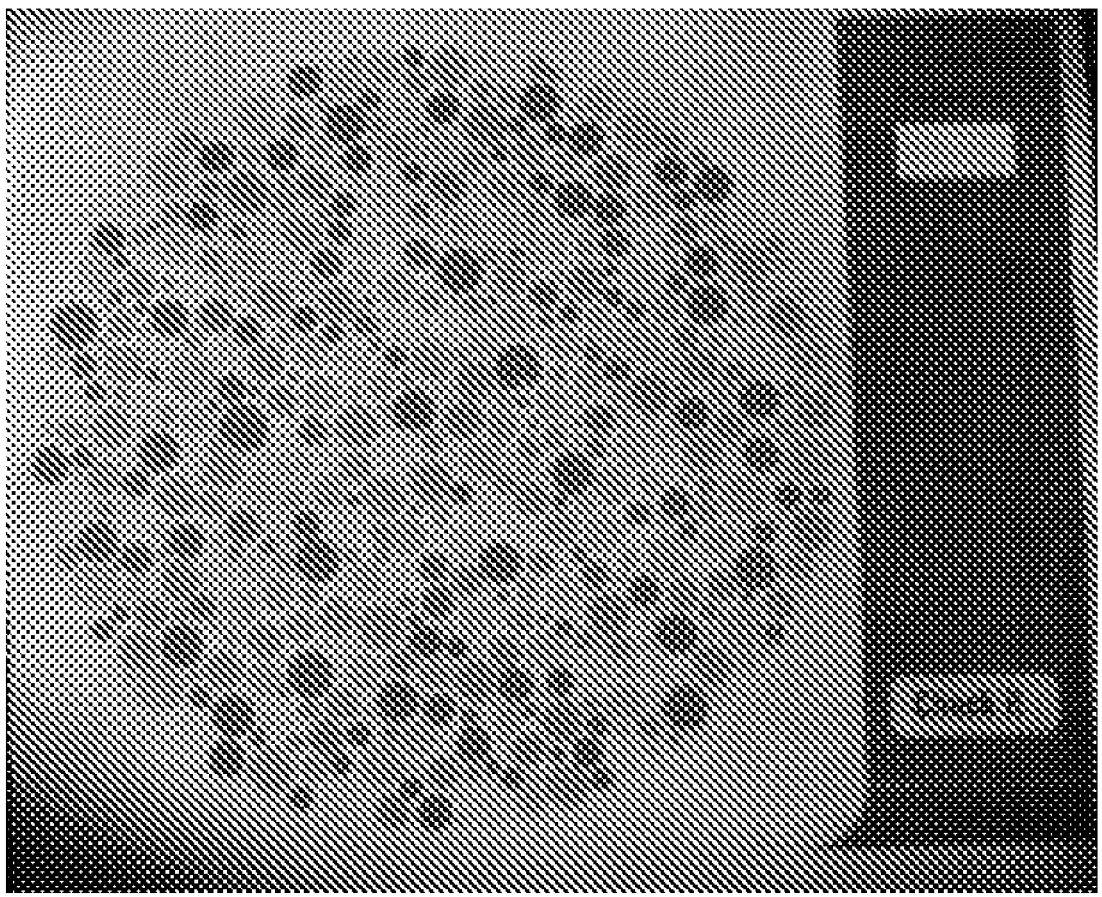
FIG. 9 is a photographic image of the color blindness test card with target number of 73 gotten at wavelength pair (510 nm, 632 nm) through a two-band mixing binocular.
Figure 10:
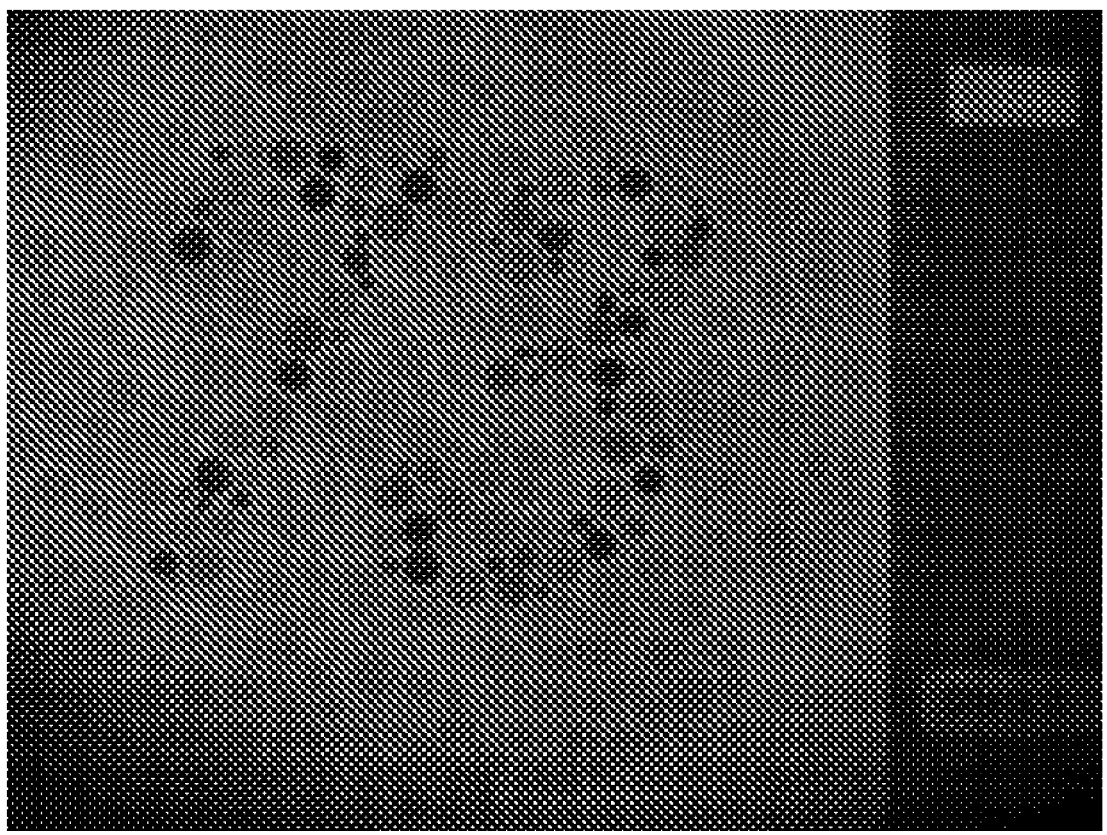
FIG. 10 is a photographic image of the color blindness test card with target number of 73 gotten at wavelength pair (470 nm, 632 nm) through a two-band mixing binocular.
Figure 11:
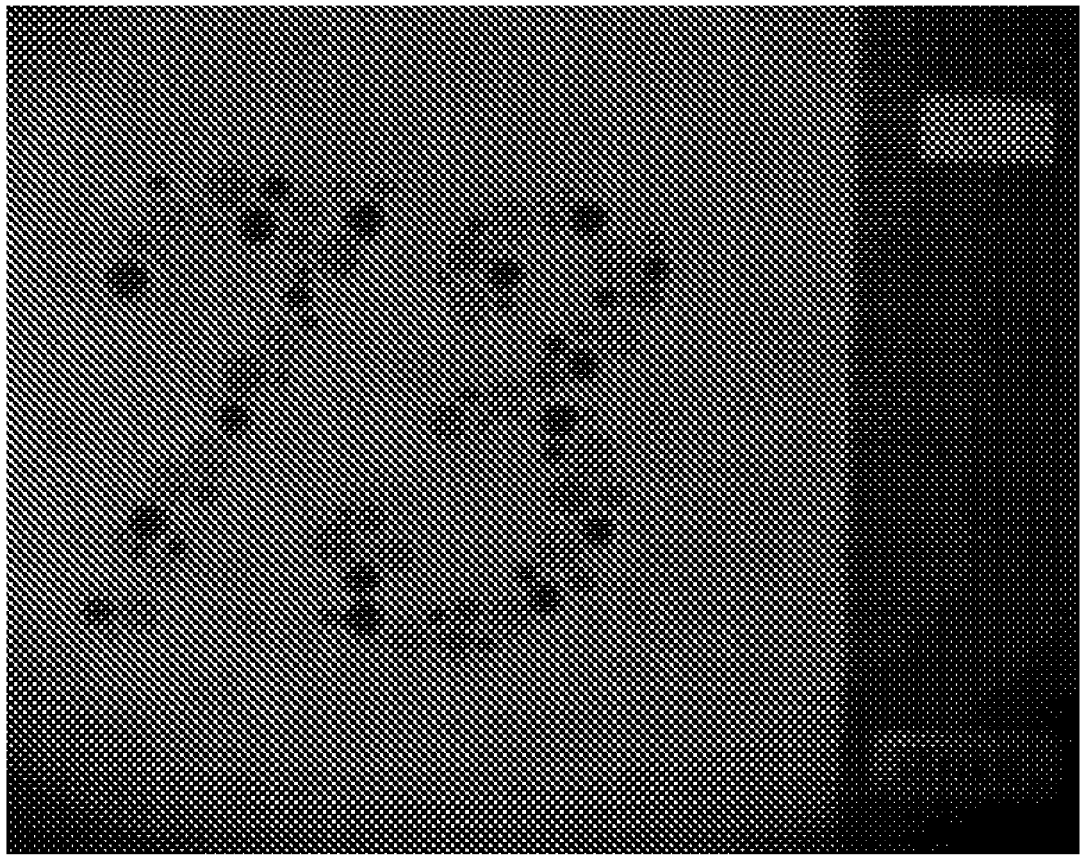
FIG. 11 is a photographic image of the color blindness test card with target number of 73 gotten at wavelength pair (620 nm, 650 nm) through a two-band mixing binocular.
Figure 12:
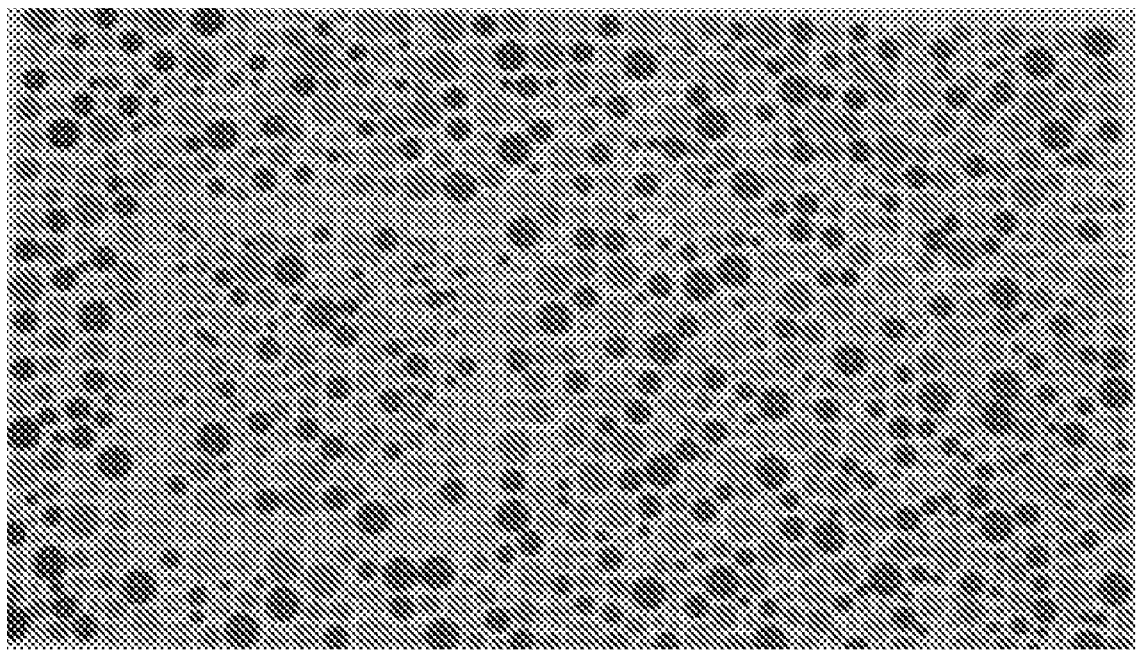
FIG. 12 is a photographic image of a color blindness test card with target figure of circle.
Figure 13:
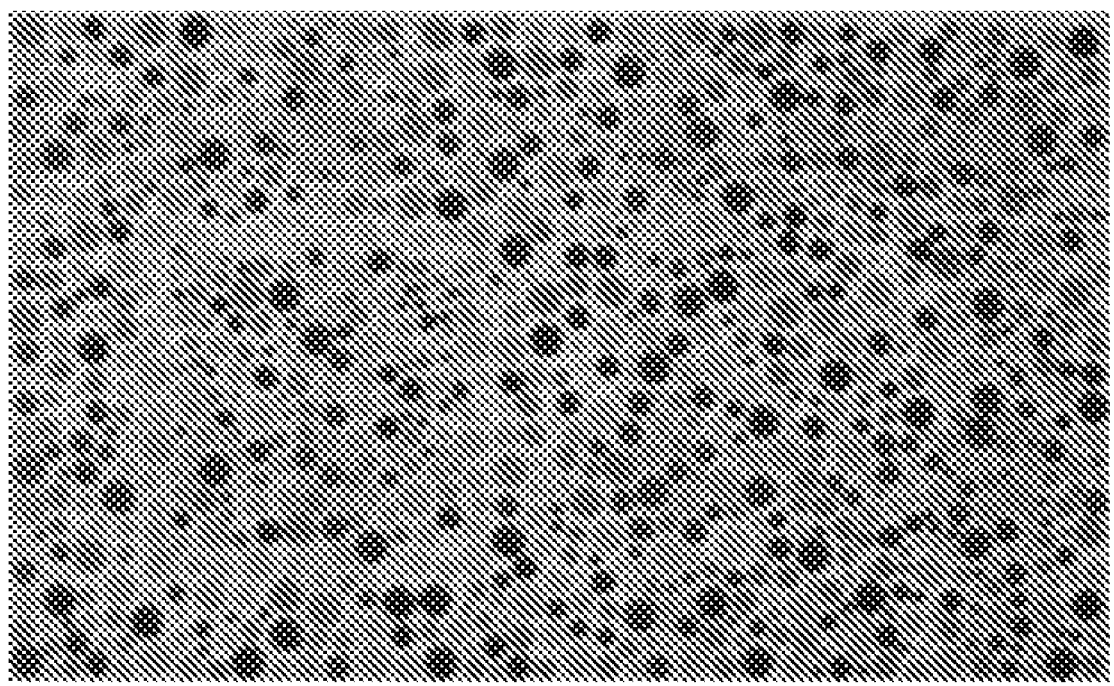
FIG. 13 is a photographic image of the color blindness test card with target figure of circle gotten at wavelength set (455 nm, 520 nm, and 632 nm).

As known, a lot of color-blindness test cards are used in the vision test for Color blindness (color vision deficiency), which is a condition in which certain colors cannot be distinguished. Here, two samples of color blindness test cards were investigated with two- and three-band mixing binocular (FIG. 5) with one kind of filter arrangement for two-band mixing (FIG. 6) and one kind of filter arrangement for three-band mixing (FIG. 7), such as described in Ding et al. [2005, Two-waveband color-mixing binoculars for the detection of wholesome and unwholesome chicken carcasses: a simulation. Applied Optics. 44(26):5454-5462] or Ding et al. [2006, Two-color mixing for classifying agricultural products for safety and quality. Applied Optics. 45(4):668-677] or Ding et al. [2006, Three-color mixing for classifying agricultural products for safety and quality. Applied Optics. 45(15):3516-3526] or Ding et al. [2005, Application of color mixing for safety and quality inspection of agricultural products. Invited paper in Optical Sensor and Sensing Systems for Natural Resources and Food Safety and Quality, Proc. SPIE 5996, 59960R]. With this two-band mixing device, the identification of targets hidden in the color blindness card (FIG. 8) are enhanced and a new image (FIG. 9) with enhanced chromaticness difference, a new image (FIG. 10) with enhanced color difference, and a new image (FIG. 11) with uniform background were gotten at the wavelength pair of (510 nm, 632 nm), (470 nm, 632 nm), and (620 nm, 650 nm), respectively. With this three-band mixing device, the identification of targets hidden in the color blindness card (FIG. 12) is enhanced and a new image (FIG. 13) with enhanced color difference at the wavelength set of (455 nm, 520 nm, 632 nm).

The results demonstrate that multi-band mixing technology provides a means to enhance the target identification by enhancing color difference and/or chromaticness difference between targets and backgrounds, and decreasing the color difference between different backgrounds. The critical finding is the two- and three-band mixing can work very well.

The light from the surface of objects is filtered by two or three-band visual device so that only the light in the wavelength range of the pass bands can pass through this visual device and reach human eyes. The color difference and/or chromaticness difference between target objects and background objects can be enhanced by these visual devices. Different color with different color attributes mean different objects. In some cases, different chromaticness, such as saturation and hue, mean different two- or three-band ratio. Then the target identification or detection, object classification can be implemented and enhanced with this visual device.

The light from the surface of objects is filtered by optical system integrated with two- and three-band mixing method so that only the light in the wavelength range of the pass bands can reach optical sensors for opto-electronic sensing devices. The color difference and/or chromaticness difference can be enhanced by these devices. And the target identification or object classification can be implemented by these devices in terms of color attributes. With this kind of opto-electronic sensing devices, two- and/or three-band ratio criteria widely used in remote sensing and machine vision applications can be calculated in terms of color attributes. With this kind of opto-electronic sensing devices, two- and/or three-band multi-spectral imaging can be acquired so that the complicated and expensive two and three band multi-spectral imaging system can be replaced by this kind of sensing devices.

The light from the lighting source is filtered by optical system integrated with two- and three-band mixing method so that only the light in the wavelength range of the pass bands can reach objects' surface. The color difference and/or chromaticness difference between target objects and background objects can be enhanced by these kinds of illumination. Under this two- or three-band mixing illumination, the color attributes of objects have relationship with two- or three-band ratio criteria widely used in remote sensing and machine vision applications. Under this two- or three-band mixing illumination, different color attributes mean different objects or different object conditions. This kind of two- or three-band mixing illumination can be used to identify, classify, and detect objects for human visual application, remote sensing, and machine vision application.

What is claimed is:

1. A method of two-band mixing or three-band mixing on a visual device comprising:
   a. integrating one-band bandpass filter(s) of central wavelength 1 and one-band bandpass filter(s) of central wavelength 2, or integrating one two-band bandpass filter of central wavelengths 1 and 2 in visual optical instruments for two-color mixing application, or
   b. integrating one-band bandpass filter(s) of central wavelength 1, one-band bandpass filter(s) of central wavelength 2, one-band bandpass filter(s) of central wavelength 3, or integrating one three-band bandpass filter of central wavelengths 1, 2, and 3 in optical instruments for three-color mixing application,
   c. illuminating the surface of objects with sufficient illumination,
   d. determining the feasible wavelength set for two- or three-band mixing application in terms of color difference, or chromaticness difference, or uniform background criterion,
   e. identifying the targets or classifying the objects by operators or inspectors using two- or three-band mixing visual device.

2. The method as described in claim 1 wherein said optical instruments comprises but not limited to telescopes, binoculars, monocular, microscope.

3. The method of claim 1 wherein said one-band, two-band, and three-band bandpass filters comprises narrow bandpass interference filters, broadband interference filters, laser line interference filters, linear variable transmittance interference filters, quality bandpass filters, and additive dichroic color filters.

4. The method of claim 1 wherein said one-band, two-band, and three-band bandpass filters comprise reflective filters as well as transmission filters.

5. The method of claim 1 wherein said one two-band bandpass filter of central wavelengths 1 and 2, and one three-band bandpass filter of central wavelengths 1, 2, and 3 comprise any shape, size, and type custom-design filter that has two pass bands with central wavelengths 1 and central wavelength 2 and three pass bands with central wavelengths 1, 2 and 3, respectively.

6. The method of claim 1 wherein said one-band bandpass filters and the method of claim 5 said any shape and size comprise any size different shape filters, such as any size of circular, rectangle, square, triangle, circle ring, ellipse, ellipse ring, trapezoid, and circular sector.

7. The method of claim 1 wherein said integrating comprises integrating a filter of two-band or three-band or filters of one-band in front of objective lenses, integrating a filter of two-band or Three-band or filters of one-band with different central wavelengths in custom design objective lenses, coating some optical component so that it can filter the light as a two-band or three band filter.

8. A method of two-band mixing or three-band mixing on optoelectronic sensing device comprising:
   a. integrating one-band bandpass filter(s) of central wavelength 1 and one-band bandpass filter(s) of central wavelength 2, or integrating one two-band bandpass filter of central wavelengths 1 and 2 in opto-electronic sensing system for two-band mixing application,
   b. integrating one-band bandpass filter(s) of central wavelength 1, one-band bandpass filter(s) of central wavelength 2, one-band bandpass filter(s) of central wavelength 3, or integrating one three-band bandpass filter of central wavelengths 1, 2, and 3 in optoelectronic sensing system for three-band mixing application,
c. illuminating the surface of objects with sufficient illumination,
d. determining the wavelength set for two-band or three-band mixing application,
e. acquiring two or three separate one-band spectral imaging by mathematic processing in terms of the signals from optical sensors,
f. identifying the targets or classifying the objects by electronic device in terms of color attributes or calculating two-band or three-band ratio criteria in terms of color attribute.

9. The method of claim 8 wherein said one-band, two-band, and three-band bandpass filters comprises narrow bandpass interference filters, broadband interference filters, laser line interference filters, linear variable transmittance interference filters, bandpass filters, and additive dichroic color filters.

10. The method of claim 8 wherein said one-band, two-band, and three-band bandpass filters comprises reflective filters as well as transmission filters.

11. The method of claim 8 wherein said one two-band bandpass filter of central wavelengths 1 and 2, and one three-band bandpass filter of central wavelengths 1, 2, and 3 comprises any shape, size, and type custom-design filter that has two pass bands with central wavelengths 1 and central wavelength 2 and three pass bands with central wavelengths 1, 2 and 3, respectively.

12. The method of claim 8 wherein said one-band bandpass filters and the method of claim 11 said any shape and size comprise any size different shape filters, such as any size of circular, rectangle, square, triangle, circle ring, ellipse, ellipse ring, trapezoid, and circular sector.

13. The method of claim 8 wherein said integrating comprises integrating a filter of two-band or three-band or filters of one-band in front of objective lenses, integrating a filter of two-band or three-band or filters of one band with different central wavelengths in custom design objective lenses, coating some optical component so that it can filter the light as a two-band or three-band filter.

14. The method of claim 8 wherein said color attributes comprises any kind of color attributes adopted for different color space, such as but not limited to R, G, B of RGB color space, hue, saturation, brightness of HSV color space, lightness, position between magenta and green, position between yellow and blue of CIELAB color space.

15. The method of claim 8 wherein said opto-electric device comprises color camera, calorimeter, novel multispectral imaging system with two- and three-color mixing, and novel spectroscopy system with two- and three-color mixing.

16. A method of two-band mixing or tree-band mixing on illumination comprising:
a. integrating one-band bandpass filter(s) of central wavelength 1 and one-band bandpass filter(s) of central wavelength 2, or integrating one two-band bandpass filter of central wavelengths 1 and 2 in illumination system for two-band mixing application,
b. integrating one-band bandpass filter(s) of central wavelength 1, one-band bandpass filter(s) of central wavelength 2, one-band bandpass filter(s) of central wavelength 3, or integrating one three-band bandpass filter of central wavelengths 1, 2, and 3 in illumination system for three-band mixing application,
c. determining the feasible wavelength set for two-band or three-band mixing application,
d. identifying the targets or classifying the objects by human vision through enhancing color difference and/or chromaticness difference or in terms of color attributes of objects corresponding to different objects or different band ratio,
e. identifying the target objects or classifying the objects by electronic device in terms of color attributes or calculating two-band or three-band ratio criteria in terms of color attributes.

17. The method of claim 16 wherein said one-band, two-band, and three-band bandpass filters comprises narrow bandpass interference filters, broadband interference filters, laser line interference filters, linear variable transmittance interference filters, commercial quality bandpass filters, and additive dichroic color filters.

18. The method of claim 16 wherein said one-band, two-band, and three-band bandpass filters comprises reflective filters as well as transmission filters.

19. The method of claim 16 wherein said one two-band bandpass filter of central wavelengths 1 and 2, and one three-band bandpass filter of central wavelengths 1, 2, and 3 comprises any shape, size, and type custom-design filter that has two pass bands with central wavelengths 1 and central wavelength 2 and three pass bands with central wavelengths 1, 2 and 3, respectively.

20. The method of claim 16 wherein said one-band bandpass filters and the method of claim 19 said any shape and size comprise any size different shape filters, such as any size of circular, rectangle, square, triangle, circle ring, ellipse, ellipse ring, trapezoid, and circular sector.

21. The method of claim 16 wherein said integrating comprises integrating a filter of two-band or three-band or filters of one-band in front of objective lenses, integrating a filter of two-band or three-band or filters of one-band with different central wavelengths in custom design objective lenses, coating some optical component so that it can filter the light as a two-band or three band filter.

22. The method of claim 16 wherein said color attributes comprises any kind of color attributes adopted for different color space, such as but not limited to R, G, B of RGB color space, hue, saturation, brightness of HSV color space, lightness, position between magenta and green, position between yellow and blue of CIELAB color space.

23. The meted of claim 16 wherein said opto-electric device comprises color camera, colorimeter, novel multispectral imaging system with two- and three-color mixing, and novel spectroscopy system with two- and three-color mixing.

* * * * *